United States Patent [19]

Chiyoda et al.

[11] 4,455,440

[45] Jun. 19, 1984

[54] METHOD FOR PRODUCING 1,3,5-TRIISOPROPYLBENZENE TRIHYDROPEROXIDES

[75] Inventors: Tsutomu Chiyoda, Toyonaka; Makoto Nakamura, Ibaraki; Shinichi Hasegawa, Otsu, all of Japan

[73] Assignee: Sumitomo Chemical Company, Limited, Osaka, Japan

[21] Appl. No.: 441,906

[22] Filed: Nov. 15, 1982

[30] Foreign Application Priority Data

Nov. 19, 1981 [JP] Japan .................... 56-186659

[51] Int. Cl.$^3$ .......................................... C07C 179/053
[52] U.S. Cl. ................... 568/565; 568/569; 568/570; 568/571
[58] Field of Search ............... 568/565, 569, 570, 571

[56] References Cited

U.S. PATENT DOCUMENTS

| D. 244,991 | 7/1977 | Weckman et al. | 222/383 |
|---|---|---|---|
| 2,664,447 | 12/1953 | Lorand et al. | 568/565 |
| 2,790,010 | 4/1957 | Shepard | 568/565 |
| 2,856,433 | 10/1958 | Thompson | 568/565 |
| 3,339,770 | 9/1967 | Weigand | 215/222 |
| 3,474,938 | 10/1969 | Clevenger | 239/333 |
| 3,978,142 | 8/1976 | Burkholder | 568/565 |
| 4,065,036 | 12/1977 | Kirk | 222/153 |
| 4,139,112 | 2/1979 | Cooke | 215/222 |
| 4,159,067 | 6/1979 | Akers | 222/153 |
| 4,161,288 | 7/1979 | McKinney | 239/333 |
| 4,204,614 | 5/1980 | Reeve | 222/153 |
| 4,227,650 | 10/1980 | McKinney | 239/333 |
| 4,345,691 | 8/1982 | Bueke | 222/153 |

FOREIGN PATENT DOCUMENTS

| 2462200 | 2/1981 | France | 220/301 |
|---|---|---|---|
| WO81/03649 | 12/1981 | World Intel. Prop. Org. | 215/222 |
| 2041339 | 9/1980 | United Kingdom | 222/153 |
| 710061 | 6/1981 | United Kingdom | 222/545 |
| 2110679 | 6/1983 | United Kingdom | 568/565 |

*Primary Examiner*—Werren B. Lone
*Attorney, Agent, or Firm*—Stevens, Davis, Miller & Mosher

[57] ABSTRACT

In a method for producing 1,3,5-triisopropylbenzene trihydroperoxides by bringing 1,3,5-triisopropylbenzene or its homologs into contact reaction with oxygen or an oxygen-containing gas in the co-existence of an aqueous alkali solution, a method for producing 1,3,5-triisopropylbenzene trihydroperoxides wherein said contact reaction is carried out under a condition that the reaction temperature be 60° to 120° C., the pH of the reaction solution phase be 8 to 11 and the amount of said aqueous alkali solution be 0.1 to 3 times by weight based on the organic layer as raw material, the reaction is finished at a point when the yield of 1,3,5-triisopropylbenzene trihydroperoxide (hereinafter referred to as THPO) is not less than 20% and besides, the total of the yield of carbinols (hereinafter referred to as THPO carbinols) having a structure in which part or all of the three hydroperoxy groups of THPO have been replaced by hydroxy groups and that of THPO above is not less than 60%, and if necessary, after separation-removing the aqueous layer from the resulting oxidation solution, the organic layer is, as such or as an organic layer containing THPO and THPO carbinols after removing reaction intermediates from it, brought into contact with hydrogen peroxide.

The 1,3,5-triisopropylbenzene trihydroperoxide are useful as a starting material of phloroglucin.

3 Claims, No Drawings

METHOD FOR PRODUCING 1,3,5-TRIISOPROPYLBENZENE TRIHYDROPEROXIDES

The present invention relates to a method for producing 1,3,5-triisopropylbenzene trihydroperoxides.

It is well known that 1,3,5-triisopropylbenzene (hereinafter referred to as TIP) is brought into contact reaction with an oxygen-containing gas in a liquid phase (East German Pat. No. 12,239, British Pat. No. 751,598), and also that 1,3,5-triisopropylbenzene trihydroperoxide (hereinafter referred to as THPO) obtained by this oxidation is decomposed with an acid, etc. to obtain phloroglucin.

But in such conventionally well-known oxidation of TIP, no interest has been shown in the formation, behaviour, etc. of by-products interest was directed toward the formation only of THPO which is a direct raw material for obtaining phloroglucin, and it was intended to inhibit the formation of by-products such as carbinols, etc.

As a result of an extensive study on the oxidation of TIP, the present inventors confirmed that, in said oxidation, various carbinols described below are formed in addition to the objective THPO: THPO precursors, i.e. 1-(2-hydroperoxy-2-propyl)-3,5-diisopropylbenzene (MHPO) represented by the formula,

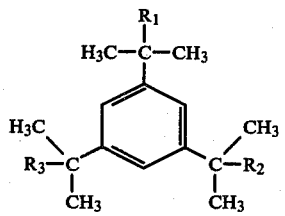

wherein $R_1=R_2=$—H and $R_3=$—OOH, and 1,3-di-(2-hydroperoxy-2-propyl)-5-isopropylbenzene (DHPO) represented by the above formula wherein $R_1=$—H, and $R_2=R_3=$—OOH, as well as the following carbinols:

MCA: $R_1=$—OH, $R_2=R_3=$—H
MCMH: $R_1=$—OH, $R_2=$—OOH, $R_3=$—H
DCA: $R_1=R_2=$—OH, $R_3=$—H
MCDH: $R_1=$—OH, $R_2=R_3=$—OOH
DCMH: $R_1=R_2=$—OH, $R_3=$—OOH
TCA: $R_1=R_2=R_3=$—OH.

As described above, in the conventional methods, no interest has been shown in using the by-products as a raw material for producing phloroglucin, and attention has been paid to only the yield of THPO. It was also confirmed by the present inventors' experiments that separation of THPO from the carbinols produced as by-products is very difficult.

For this reason, the present inventors made a further study on the by-products in this oxidation, and as a result, found that carbinols such as MCDH, DCMH and TCA (hereinafter referred to as THPO carbinols), if not separated from THPO, will convert to THPO by applying further oxidation treatment in the presence of THPO, and therefore that, in the oxidation of TIP, not only the yield of THPO but also those of both THPO and THPO carbinols have a very important significance. As a result of a further investigation, the present inventors found that, by carrying out the oxidation under specified reaction conditions and finishing at a point when a specified yield or more has been reached, the total of THPO and THPO carbinols can be obtained with very good efficiency. The present invention was completed based on this finding.

According to the present invention, the following method is provided: In the method for producing 1,3,5-triisopropylbenzene trihydroperoxides by bringing 1,3,5-triisopropylbenzene or its homologs into contact reaction with oxygen or an oxygen-containing gas in the presence of an aqueous alkali solution, a method for producing 1,3,5-triisopropylbenzene trihydroperoxides wherein said contact reaction is carried out under conditions such that the reaction temperature is 60° to 120° C., the pH of the reaction solution phase is 8 to 11 and the amount of said aqueous alkali solution is 0.1 to 3 times by weight based on the organic layer as raw material, and the reaction is finished at a point when the yield of 1,3,5-triisopropylbenzene trihydroperoxide is not less than 20% and besides, the total of the yield of carbinols having a structure in which part or all of the three hydroperoxy groups of THPO have been replaced by hydroxy groups and that of THPO above is not less than 60%.

Thus, according to the present invention, the oxidation products for a marked improvement in the final THPO yield can be obtained advantageously and in high yields.

The present inventors further found that oxidation with hydrogen peroxide is very useful for obtaining THPO from the foregoing THPO carbinols, and therefore that combining the foregoing two oxidations is very useful for finally obtaining THPO in good yields. The present invention was completed based on this finding.

According to the present invention, the following second method is provided: In the method for producing 1,3,5-triisopropylbenzene trihydroperoxides by bringing 1,3,5-triisopropylbenzene or its homologs into contact reaction with oxygen or an oxygen-containing gas in the presence of an aqueous alkali solution, a method for producing 1,3,5-triisopropylbenzene trihydroperoxides wherein said contact reaction is carried out under conditions such that the reaction temperature is 60° to 120° C., the pH of the reaction solution phase is 8 to 11 and the amount of said aqueous alkali solution is 0.1 to 3 times by weight based on the organic layer as raw material; the reaction is finished at a point when the yield of 1,3,5-triisopropylbenzene trihydroperoxide is not less than 20% and besides, the total of the yield of carbinols having a structure in which part or all of the three hydroperoxy groups of THPO have been replaced by hydroxy groups and that of THPO above is not less than 60%, and after separating the aqueous layer from the resulting oxidation solution, the organic layer is, as such or as an organic layer containing THPO and THPO carbinols after removing reaction intermediates from it, brought into contact with hydrogen peroxide.

According to the method of the present invention, THPO is obtained in very high yields from TIP and homologs thereof, so that this method is very superior as a method for producing THPO.

Next, the present invention will be illustrated in detail.

In the present invention, the starting material used for the oxidation with oxygen or an oxygen-containing gas (e.g. air) is 1,3,5-triisopropylbenzene or its homologs.

The term "homolog" referred to herein means THPO precursors such as MHPO and DHPO which are generally recycled as intermediates produced by the oxidation. In general, as the starting material, 1,3,5-triisopropylbenzene is used alone or in mixtures with its homolog, but the homolog alone may be used.

In this oxidation, the pH of the liquid phase in the contact reaction is a factor exerting an influence on the reaction time and the composition of oxidation oil, so that it is necessary to control the pH in the liquid phase within a range of 8 to 11.

When the pH is below 8, the radical chain reaction is markedly disturbed by by-products such as alkylphenols, organic acids, etc. When the pH exceeds 11, carbinols such as MCA, MCMH, DCA, etc. are formed markedly, thus lowering the formation of THPO and THPO carbinols.

In the pH range of 8 to 11 specified in the present invention, with an increase in the pH, the rate of reaction becomes fast and also conversion of the formed THPO to THPO carbinols becomes rapid, as a result of which the proportion of THPO carbinols in the objective product tends to become high. When the pH is lower, the yield and proportion of THPO becomes high, but the reaction time tends to become long. In the present invention, therefore, it is more preferred to control the pH within a range of 9 to 10. For controlling the pH, a method is generally employed in which an alkali is added to the reaction system with the progress of reaction so as to maintain the above-mentioned pH range.

The amount of aqueous alkali solution used is 0.1 to 3 times by part in weight based on the organic layer, a raw material, from the standpoints of the yield, reaction time or volume efficiency of reactor.

When water is not used in the oxidation system, the formation of by-products is remarkable, thus resulting in a reduction in the yield.

Also, from the standpoint of safety on reaction or pH control in the liquid phase, the amount of aqueous alkali solution used needs to be not less than 0.1 time in part by weight based on the organic layer, a raw material.

To use the aqueous alkali solution in excess based on the organic layer, a raw material, has the effect of improving the selectivity of the objective compound. It is therefore not much preferred in this respect as well as in terms of the volume efficiency of reactor.

For the reason described above, it is more preferred that the amount of aqueous alkali solution used in the present invention is within a range of 0.2 to 1.5 times by part in weight based on the organic layer, a raw material.

The reaction temperature is generally 60° to 120° C., more preferably 80° to 100° C., because the rate of reaction becomes slow at lower temperatures, and because formation of carbinols increases at higher ones.

The oxidation is carried out under the three specified conditions described above, that is, the pH of the reaction solution phase, reaction temperature and amount of the aqueous alkali solution used, but, also, the end point of the reaction is made a point at which the yield of THPO is not less than 20% and besides, the total of the yields of both THPO and THPO carbinosl is not less than 60%.

When the oxidation is carried out under the conditions of the present invention, THPO is produced through MHPO and DHPO. Since, however, this reaction is a consecutive reaction and once formed THPO converts to THPO carbinols in the oxidation system, the THPO yield in said oxidation reaches a maximum at a certain point and then lowers in the course of the progress of reaction, which does not result in the yield increasing with the progress of reaction like many chemical reactions. The amount of THPO carbinols formed begins to increase after the formation of THPO while being accompanied by other side reactions.

Since the present invention is intended to obtain both THPO and THPO carbinols in good yields, it is necessary for such oxidation system that, independently of whether the THPO yield is in the course of increase or decrease, the end point of the reaction is made a point at which the THPO yield is not less than 20% and besides, the total of the yields of both THPO and THPO carbinols is not less than 60%. If the total of the yields of both components is not less than 60%, when the THPO yield is less than 20%, the reaction proceeds too much and oxidation efficiency becomes poor, and besides, the subsequent oxidation with hydrogen peroxide becomes disadvantageous.

Thus, both THPO and THPO carbinols can be obtained in good yields.

According to the present invention, there is provided the second method in which the thus obtained oxidation solution containing THPO and THPO carbinols is further treated with hydrogen peroxide to convert THPO carbinols to THPO whereby THPO is finally produced in good yields.

For treating the oxidation solution with hydrogen peroxide, the aqueous alkali layer of the solution is previously removed by optional means such as liquid/liquid separation (hereinafter, the term "oxidation solution" means the oily layer after removal of the aqueous layer).

This oxidation solution is, as such or after intermediates such as MHPO, DHPO, etc. have previously been removed from it by extraction or recrystallization, brought into contact with hydrogen peroxide. The separated intermediates are generally recycled as a raw material for oxidation. In contact with hydrogen peroxide, the oxidation solution or the same after removal of the intermediates may be dissolved in an organic solvent. As the organic solvent, those which will not react with hydrogen peroxide and besides completely dissolve THPO and THPO carbinols, are preferred. For example, halogenated hydrocarbons and ethers are suitable. Solvents which will not dissolve THPO and THPO carbinols at all are also usable, but they are not preferred in terms of yield and operation.

In this reaction, hydrogen peroxide is generally used in a solution of 10 to 50% by weight in concentration, and the amount of the solution is 1.5 to 10 times by equivalent, converted to hydrogen peroxide, based on the carbinol group of THPO carbinols. In this reaction, acidic catalysts such as sulfuric acid, hydrochloric acid, perchloric acid, phosphoric acid, etc. are also used, and their amount is generally 0.05 to 0.5 mole/liter aqueous hydrogen peroxide solution.

The reaction temperature in this reaction is generally 30° to 100° C.

Thus, THPO is formed by reacting THPO carbinols in the oxidation solution with hydrogen peroxide. THPO present in the oxidation solution is almost inert to this reaction, which therefore results in that THPO is finally obtained in good yields from 1,3,5-triisopropylbenzene or homolog thereof.

Next, the present invention will be illustrated with reference to the following examples.

EXAMPLE 1

To a reactor were added 204 g of 1,3,5-triisopropylbenzene (TIP), 204 g of water and 2 g of a recycle oxidation oil, followed by heating to 94° to 96° C. Thereafter, auto-oxidation was carried out while blowing oxygen through the solution from the inlet pipe at a constant rate with stirring and at the same time adding a conc. aqueous caustic soda so that the pH in the reaction solution was 9.5±0.4.

After beginning of the reaction, the reaction solution was sampled at regular time intervals, and THPO and THPO carbinols were analyzed to obtain the respective yields. The results as shown in Table 1 were obtained.

TABLE 1

| Oxidation time (hr) | Yield of THPO (%) | Total yield (%)* |
|---|---|---|
| 15 | 2.5 | 2.5 |
| 25 | 25.0 | 35.0 |
| 35 | 30.5 | 62.0 |
| 45 | 31.5 | 80.0 |
| 55 | 26.5 | 85.5 |
| 65 | 20.0 | 80.0 |

*Show the total of the yields of THPO and THPO carbinols.

In the method of the present invention, the oxidation can be finished at any point between 35 hours and 65 hours after beginning of the oxidation.

EXAMPLE 2

Auto-oxidation was carried out in the same manner as in Example 1 except that the pH in the reaction solution was adjusted with a conc. aqueous caustic soda so as to maintain a range of 8.5±0.4. By carrying out analysis in the same manner, the results shown in Table 2 were obtained.

TABLE 2

| Oxidation time (hr) | Yield of THPO (%) | Total yield (%) |
|---|---|---|
| 30 | 10.0 | 10.0 |
| 45 | 25.0 | 30.0 |
| 60 | 30.0 | 45.0 |
| 75 | 35.0 | 65.0 |
| 90 | 35.0 | 85.0 |
| 105 | 30.0 | 85.0 |

In the method of the present invention, the reaction can be finished at any point 75 hours after beginning of the reaction.

EXAMPLE 3

Auto-oxidation was carried out in the same manner as in Example 1 except that the pH in the reaction solution was adjusted with a conc. aqueous caustic soda so as to maintain a range of 10.5±0.4. By carrying out analysis in the same manner, the results shown in Table 3 were obtained.

TABLE 3

| Oxidation time (hr) | Yield of THPO (%) | Total yield (%) |
|---|---|---|
| 15 | 10.0 | 15.0 |
| 25 | 25.0 | 50.0 |
| 35 | 25.0 | 75.0 |
| 45 | 20.0 | 85.0 |
| 55 | 10.0 | 80.0 |

In the method of the present invention, the reaction can be finished at any point between 35 hours and 45 hours after beginning of the reaction.

COMPARATIVE EXAMPLE 1

Auto-oxidation was carried out in the same manner as in Example 1 while adjusting the pH in the reaction solution with a conc. aqueous caustic soda so as to maintain ranges of 7.5±0.4 and 11.5±0.4. By carrying out analysis in the same nanner, the results shown in Tables 4 and 5 were obtained.

TABLE 4

| pH = 7.5 ± 0.4 | | |
|---|---|---|
| Oxidation time (hr) | Yield of THPO (%) | Total yield (%) |
| 60 | 5.0 | 5.0 |
| 90 | 15.0 | 20.0 |
| 120 | 25.0 | 35.0 |
| 150 | 25.0 | 45.0 |
| 180 | 20.0 | 50.0 |

TABLE 5

| pH = 11.5 ± 0.4 | | |
|---|---|---|
| Oxidation time (hr) | Yield of THPO (%) | Total yield (%) |
| 15 | 5.0 | 20.0 |
| 25 | 10.0 | 35.0 |
| 35 | 5.0 | 45.0 |
| 45 | 3.0 | 38.0 |

EXAMPLE 4

204 Grams of TIP, 40.8 g of water and 2 g of a recycle oxidation oil were added to a reactor, and auto-oxidation was carried out in the same manner as in Example 1. By carrying out analysis in the same manner, the results shown in Table 6 were obtained.

TABLE 6

| Oxidation time (hr) | Yield of THPO (%) | Total yield (%) |
|---|---|---|
| 15 | 5.0 | 7.0 |
| 25 | 25.0 | 40.0 |
| 35 | 25.0 | 75.0 |
| 45 | 20.0 | 80.0 |
| 55 | 15.0 | 75.0 |
| 65 | 10.0 | 65.0 |

In the method of the present invention, the reaction can be finished at any point between 35 hours and 45 hours after beginning of the oxidation.

EXAMPLE 5

204 Grams of TIP and 612 g of water were added to a reactor, and auto-oxidation was carried out in the same manner as in Example 1. By carrying out analysis in the same manner, the results shown in Table 7 were obtained.

TABLE 7

| Oxidation time (hr) | Yield of THPO (%) | Total yield (%) |
|---|---|---|
| 25 | 5.0 | 5.0 |
| 35 | 15.0 | 20.0 |
| 45 | 30.0 | 45.0 |
| 55 | 35.0 | 65.0 |
| 65 | 37.0 | 85.0 |
| 75 | 35.0 | 85.0 |

In the method of the present invention, the reaction can be finished at any point 55 hours after beginning of the oxidation.

EXAMPLE 6

In the method of Example 1, from the oxidation mixture, as obtained by finishing the raection 55 hours after beginning of the oxidation, was separated the aqueous layer, and an aqueous alkali solution was added to the resulting oxidation oil layer which was then separated into the oily and aqueous layers. The aqueous alkali layer was neutralized and extracted with dichloroethane to separate intermediates (MHPO, DHPO, etc.). The dichloroethane solution obtained here consisted of 8 parts by weight of THPO, 11 parts by weight of THPO carbinols and 78 parts by weight of dichloroethane.

To 100 g of this dichloroethane solution was added 39.5 g of an aqueous solution (5 equivalents based on the carbinol group) containing 20% by weight of hydrogen peroxide and 1% by weight of sulfuric acid, followed by reaction at 60° to 65° C. for 4 hours. THPO carbinols were hardly detected in the reaction product obtained, and the yield of THPO at that time was 84.2% Hereupon, the yield of THPO is a value based on the total of the fed THPO and THPO carbinols.

EXAMPLE 7

In the method of Example 1, from the oxidation mixture, as obtained by finishing the reaction 55 hours after beginning of the oxidation, was separated the aqueous layer, and the resulting oxidation oil layer was dissolved in dichloroethane.

The composition of this solution consisted of 8 parts by weight of THPO, 11 parts by weight of THPO carbinols and 81 parts by weight of dichloroethane and others.

To 100 g of this dichloroethane solution was added 50 g of an aqueous solution (5 equivalents based on the carbinol group) containing 20% by weight of hydrogen peroxide and 1% by weight of sulfuric acid, followed by reaction at 60° to 65° C. for 5 hours. THPO carbinols were hardly detected in the reaction product obtained, and the yield of THPO at that time was 80%. Hereupon, the yield of THPO is a value based on the total of the fed THPO and THPO carbinols.

What is claimed is:

1. A method for producing 1,3,5-triisopropylbenzene trihydroperoxides which comprises bringing 1,3,5-triisopropylbenzene or its homologs into contact reaction with oxygen or an oxygen-containing gas in the presence of an aqueous alkali solution, wherein said contact reaction is conducted at a reaction temperature of 60° to 120° C., the pH of the reaction solution phase is 8 to 11 and the amount of said aqueous alkali solution is 0.1 to 3 times by weight based on the organic layer as raw material, and wherein the reaction is finished at a point when the yield of 1,3,5-triisopropylbenzene trihydroperoxide (THPO) is not less than 20% and the total of the yield of THPO carbinols having a structure in which part or all of the three hydroperoxy groups of THPO have been replaced by hydroxy groups and that of THPO is not less than 60%.

2. A method according to claim 1 wherein after the finish of the reaction, the aqueous layer present is separated from the resulting oxidation solution, and the organic layer containing THPO and THPO carbinols is contacted with hydrogen peroxide.

3. A method according to claim 2 wherein before contacting the organic layer with hydrogen peroxide, reaction intermediates are removed from the organic layer.

* * * * *